United States Patent [19]

Grychowski et al.

[11] Patent Number: 5,054,478
[45] Date of Patent: Oct. 8, 1991

[54] NEBULIZER

[75] Inventors: Jerry R. Grychowski, Lake Zurich; Alfred G. Brisson, Kildeer; Exequiel D. Cruz, Arlington Heights; Christopher Nowacki, Long Grove, all of Ill.

[73] Assignee: Trudell Medical, London, Canada

[21] Appl. No.: 341,794

[22] Filed: Apr. 21, 1989

[51] Int. Cl.⁵ .......................................... A61M 11/00
[52] U.S. Cl. ........................ 128/200.21; 128/204.25; 128/200.14; 128/203.12
[58] Field of Search .................... 128/200.21, 204.25, 128/200.14, 203.12

[56] References Cited

U.S. PATENT DOCUMENTS

| 3,913,843 | 10/1975 | Cambio, Jr. | 128/200.21 X |
| 4,461,735 | 7/1984 | Wirt | 128/204.13 X |
| 4,911,157 | 3/1990 | Miller | 128/200.21 |

Primary Examiner—Edgar S. Burr
Assistant Examiner—E. P. Raciti
Attorney, Agent, or Firm—Robert M. Wolters

[57] ABSTRACT

A nebulizer has a body with oxygen inlet and outlet ends through which oxygen flows. An aspirator is provided within the body in communication with a water supply conduit for aspirating water into oxygen flowing through the body. A float valve interconnects the water inlet and the aspirator for controlling the flow of water into the oxygen flowing through the nebuliz

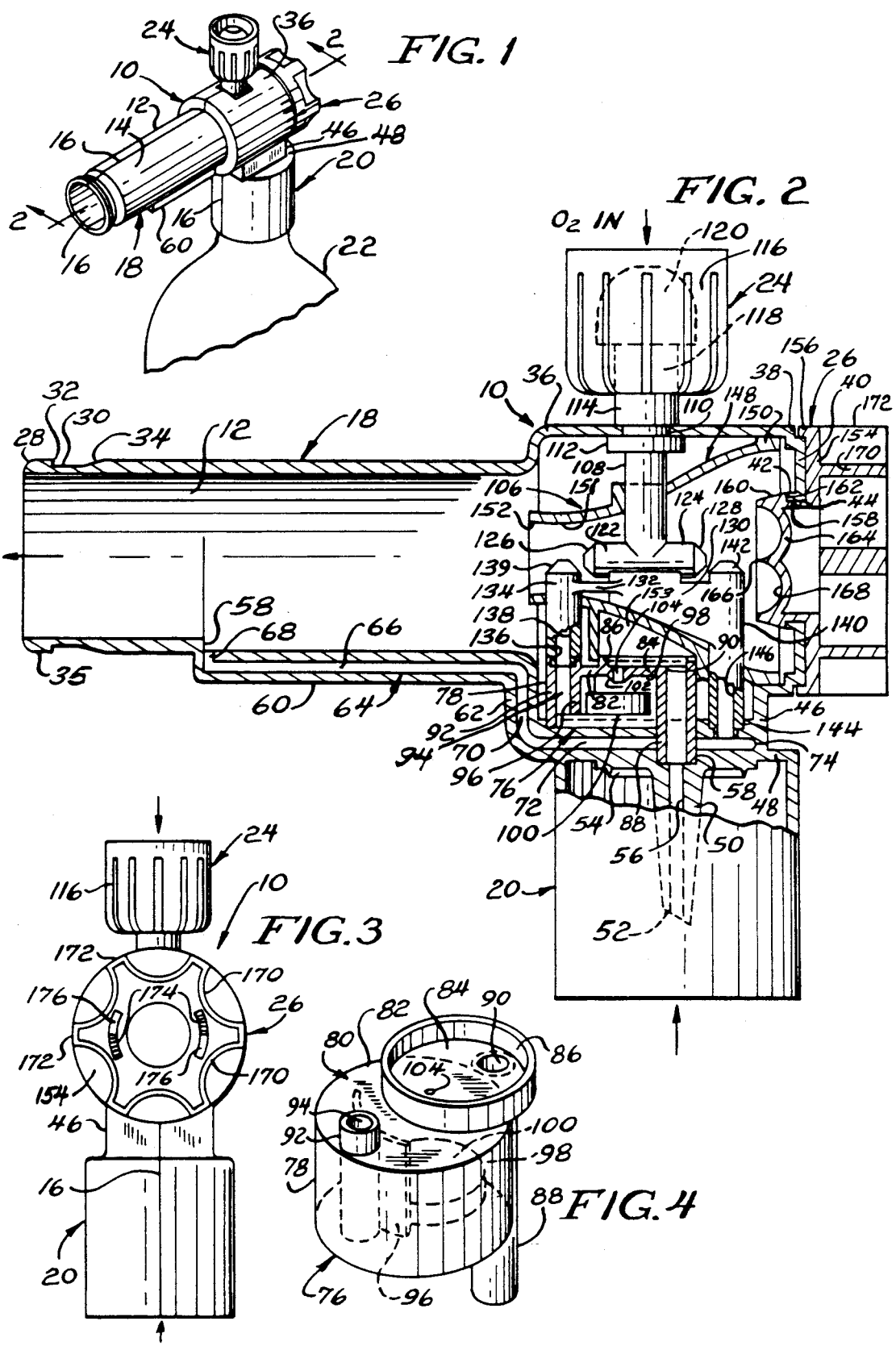

NEBULIZER

BACKGROUND OF THE INVENTION

It is common practice to supply oxygen to patients in hospitals and in nursing homes. The oxygen may be supplied to the patient by introducing it into an oxygen tent in which the upper portion of the patient's body and head are located, or by means of a mask, or by means of one or more nasal tubes. It is sometimes desired to introduce water vapor into the oxygen supplied to the patient, and it may also be desired to introduce a certain amount of ambient air along with the oxygen to reduce the percentage of oxygen breathed by the patient.

Nebulizers are known for introducing water vapor into oxygen supplied to a patient. Nebulizers known to us utilize a rigid bottle of sterile water. Such bottles of water are a special-order item and are expensive. Consideration has been given to utilizing sterile water supplied in a flexible bag of water. This presents problems in that if the bag is hung below the nebulizer and the water is aspirated into the oxygen there will be one flow rate, whereas if the bag is hung upside down at a higher level as is common practice in hospitals, then there will be gravitational flow and a much larger quantity of water will be supplied to the nebulizer for incorporation as water vapor in the oxygen.

OBJECTS AND SUMMARY OF THE PRESENT INVENTION

It is an object of the present invention to provide a nebulizer for introducing water vapor into oxygen supplied to a patient in which the water is introduced from a flexible bag that may be above or below the nebulizer.

It is a further object of the present invention to provide a nebulizer for introducing water vapor into oxygen supplied to a patient in which water that is not fully evaporated into the oxygen is recirculated.

Yet another object of the present invention is to provide a nebulizer for introducing water vapor into oxygen supplied to a patient wherein air is introduced to dilute the oxygen supplied to the patient.

In achieving the foregoing and other objects, we provide a nebulizer in which water is aspirated into a float chamber, and in which the water may be also supplied gravitationally with the float blocking flow of water into the float chamber when a predetermined level is reached.

The nebulizer presented herein is provided with at least two aspirators whereby water vapor can be evaporated into the flow of oxygen supplied to a patient, and whereby drain water can be recirculated and further aspirated into the oxygen supply. A third aspirator may be supplied, or the aspirating chamber of the nebulizer may be so shaped that the first two aspirators produce a negative pressure relative to ambient air, whereby to bleed air into the oxygen supplied.

THE DRAWINGS

The present invention will be best understood with reference to the following specification when taken in connection with the accompanying drawings wherein:

FIG. 1 is a perspective view showing the aspirator of the present invention as mounted on a bottle or bag of water;

FIG. 2 is a longitudinal sectional view on an enlarged scale as taken substantially along the line 2—2 in FIG. 1;

FIG. 3 is a right-end view on a scale reduced with reference to FIG. 2; and

FIG. 4 is a perspective view of the float chamber.

DETAILED DISCLOSURE OF THE ILLUSTRATED EMBODIMENT

A nebulizer 10 constructed in accordance with the present invention is shown in FIGS. 1-3. The nebulizer is made of plastic resin moldings of suitable material, and includes two body shells 12 and 14 of mirror image shape about a vertical plane and joined together along seams 16 by suitable means such as sonic or solvent welding. The nebulizer includes a cylinder 18 extending to the left and shaped for accommodation to a flexible hose leading to the patient. The nebulizer further has a depending cylindrical fitting 20 which may be internally threaded for receipt of a bottle or bag 22 of sterile water. The bag may be rigid or flexible. The nebulizer further includes an oxygen inlet fitting 24 and an air bleed adjustment knob 26.

The outer end of the tubular portion 18 is rounded off at 28 for receipt of a tube extending from the nebulizer 10 to the patient. A reduced neck portion 30 is provided inwardly a short distance from the rounded outer end 28, being defined relatively adjacent the outer end by a right-angle shoulder 32, and by a tapered section 34. The rounded outer end 28 and the right-angle shoulder 32 between them define a ring 35 over which a fitting on the tube leading to the patient extends, fitting within the reduced neck portion 30 to retain the hose in position. At the opposite end of the cylinder or tubular portion 18 there is integrally joined a cylindrical body 36 which is of slightly larger diameter than the tubular portion 18. At the right end of the body (as viewed in FIG. 2) there is an indentation or step 38 from which a wall 40 perpendicular to the axis of the body 36 extends radially inwardly. At its inner margin the wall 40 is provided with an axially inwardly directed flange 42 defining a circular opening 44.

The cylindrical fitting 20 is formed integral with a downward extension 46 of the body, the cylinder 20 having a top horizontal wall 48. A tapered pin 50 depends from the wall 48 and has an oblique lower end 52 providing a sharp lower edge for puncturing the puncturable seal at the top of the water bottle or bag 22. The fitting 20 may be internally threaded. Alternatively, when it is desired to hang a flexible water bag upside down above the nebulizer a tube from the bottle is received over the tapered pin 50. An outwardly spaced annular rib 54 extends downwardly from the wall 48 to interfit with the top end of the bottle or bag 22 when the bottle or bag is positioned below the nebulizer. The tapered pin 50 is provided with a central bore 56 extending from the lower end thereof up into and partially through the wall 48 where it communicates with a counter bore 57.

Relatively toward the left end of the tubular or cylindrical member 18 there is provided an internal step 58, and a depending longitudinal extension 60 runs from just beyond the step along the lower median line of the tubular member 18 through a continuing but depending extension 62 on the front of the body 36 and the extension 46 thereof. The tubular member 18 is provided with a flow passage 64 which extends longitudinally through the extension 60 at 66, and then radially inwardly at 68 to communicate with the interior of the tubular member 18 immediately adjacent the step 58. The flow passage 64 at the right end of the horizontal portion thereof at 66 depends at 70 in the depending extension 62, and then extends horizontally at 72 through the depending body extension 46 to a termination at 74 adjacent the right end of the depending extension 46.

The body 36 is provided internally thereof with a float chamber 76 seen in FIGS. 2 and 4. The float chamber 76 includes an outer cylindrical wall 78 and has a top wall 80 which includes a relatively large diameter circular section 82 and an overlapping smaller circular section 84. An axially upstanding circular rim 86 is provided about the smaller circular section 84 of the top wall. An integral, axially-extending filler tube 88 extends from the top wall 80, a portion of the wall thereof being common with the cylindrical wall 78. The tube 88 depends below the circular wall 78. A circular opening 90 in the top wall smaller diameter circular portion 84 communicates with a bore extending through the filler tube 88.

A water aspiration tube 92 extends above the larger diameter circular portion 82 of the top wall 80 and extends nearly to the bottom of the float chamber 76, being disposed diametrically opposite from the filler tube 88. An axial bore 94 extends through the tube 92 from end to end thereof. A portion of the wall of the tube 92 is common with the wall 78 of the float chamber 76. An arcuate baffle 96 is in part common with the wall of the tube 92, and extends from the bottom of the tube 92 up to the wall 80, particularly the larger diameter circular section 82 thereof. The baffle 96 is a section of a cylinder, being straight in its vertical direction, and curved in its horizontal dimension, being concave to the right as seen in FIGS. 2 and 3.

The arcuate baffle 96 and the opposite portion of the wall 78 of the cylinder define with the top wall 80 a float cell 98 in which there is disposed a float 100. The float 100 is of rather shallow height, being of cylindrical shape and having flat top and bottom surfaces. The float is of a character such that it will float in water, and may be of an expanded foam plastic resin construction, such as foam polystyrene. The external surfaces are smooth, and this may be an inherent characteristic of the foam plastic material, or a plastic sealing film may be bonded thereto in any suitable manner. Alternatively, the float could be of a smooth plastic construction and hollow on the inside, filled with air, so that it will float. A hollow metal cylinder is also a possibility, but does not appear to be economical as compared with either a hollow plastic cylinder, or an expanded foam plastic resin cylinder. The wall 84 is provided with a downward tapered thickening or extension 102 FIG. 2, and a bore 104 extends vertically through the wall 84 and the extension 102, the latter thereby forming a valve seat for the valve float 100.

Also mounted within the body 36 and suitably secured thereto as by solvent or sonic welding is an aspirator molding 106 having an upstanding hollow stem 108 pivoted therein and extending out through a hole 110 in the top portion of the housing along the seam 16. An annular flange 112 on the stem 108 underlies the adjacent portion of the body 36, while an enlargement 114 on the stem 108 overlies the adjacent portion of the body to locate the aspirator molding. The oxygen tubing connection 24 includes an upwardly opening cup 116 above the enlargement 114, and an enlarged axial extension 118 of the stem 108 having an enlarged, and rounded head 120 for connection of an oxygen hose or tube extending from a flow meter, and in turn supplied by an oxygen source such as a bottle of compressed oxygen. Conventional connections may be used at this point and are not shown in detail.

At the bottom of the tube 108 there is a pair of generally oppositely disposed jet nozzles 122 and 124. A hollow bore extends through the nozzles, the nozzles being tapered at the tips respectively at 126 and 128. The hollow bore through the nozzles communicates with the hollow bore through the tube 108, so that oxygen is blown out of the nozzle 122 forwardly (to the left) while oxygen is blown out of the nozzle 128 rearwardly (to the right).

A wall 130 depends from the nozzles 122 and 124, and has a forward extension 132 which supports a vertical aspirating nozzle 134. The bottom end of the nozzle 134 is stepped at 136 and cooperates with a complimentary step at the top of the tube 92. The aspirating nozzle 134 is provided with a hollow bore 138, and the upper end or tip thereof is frustoconical at 139. As a result, oxygen blowing out of the nozzle 122 passes directly above the tip of the nozzle 134 and aspirates water up from the float cell 98 for introducing water vapor into the stream of oxygen.

The wall 130 at the right or rear end supports a vertical aspirating nozzle 140 having a tapered upper end 142, and a lower end which extends down into the depending portion 46, being seated in a complimentary aperture 144. The aspirating nozzle 140 is provided with a hollow axial bore 146, and this communicates with the horizontal run 72 of the water return passage 64. The upper end of the aspirating tube 140 is disposed substantially in alignment with the rearwardly directed oxygen nozzle 124. Water that is not fully vaporized into oxygen collects at the step 58 and returns through the bore 64, and is aspirated through the nozzle 140 for reevaporation into the oxygen.

The aspirator molding 106 is completed by a shroud 148 which is coaxial with the oxygen nozzles 122 and 124. The shroud is of a maximum diameter at the right end and has a thickened rim 150 that seats within the body 36. The shroud then tapers inwardly at a nonuniform rate, initially tapering at a fairly shallow angle, then steeper, and then again more shallow to a point of minimum diameter 151 substantially aligned with the aspirating nozzle 134. The shroud then tapers outwardly slightly to an outlet diameter 152 of larger diameter than the minimum diameter 150. A depending cylinder 153 on the shroud cooperates with the wall 86 to form a sealing lid for aspirating water up within the wall 86 to form a pool of water draining into the float chamber through orifice 104.

The air bleed control knob 26 comprises a circular flat wall 154 fitting against the wall 40 of the body 36. An annular peripheral flange 156 extends to the left and is received in the stepped portion 38 of the housing body 36. The knob further is provided with a central cylindrical portion 158 coaxial with the oxygen nozzles 122 and 124, and which extends through the central opening 44 in the wall 40 past the flange 42. The cylindrical portion 158 is provided with a tapered tip 160 providing a right-angle shoulder 162 so that the tip may snap past the flange 52 and lock in place with the shoulder 162 at the end of the flange.

Centrally of the cylindrical portion the knob is provided with a semi-toroidal wall 164 providing a central, axial point 166, and an annular depression 168 having a semi-circular longitudinal section.

Accordingly, oxygen from the nozzle 124 strikes the point 166, and is reversed in direction to pass into the shroud 148, and then to pass out at the left or exit end 152 of the shroud 148.

At the right or outer end the knob 26 is provided with a succession of relieved or scalloped flanges 170 which are concave radially outwardly, and which join at a plurality of substantially flat-topped peripheral junctures 172. The flanges 170 and junctures 172 provide for finger and thumb grip for rotating the knob relative to the body 136. The wall 154 of the knob is provided with a pair of arcuate slots 174 extending axially through the knob wall and alignable slots 176 in the body wall 40. Greater or lesser alignment is produced upon rotation of the knob, whereby greater or lesser amounts of air can be sucked into the shroud 148 to dilute the oxygen exiting from the nozzles 122 and 124.

Reversal of oxygen flow from the nozzle 124 by the semi-toroidal surface 168, and direction of the nozzle 122 to the left in FIG. 2 insures that oxygen will pass from the exit ends 152 of the shroud, thereby producing a negative pressure outwardly of the flange 42, whereby a certain amount of air will be drawn in through the slots 176, the precise amount being determined by the rotational positioning of the knob, and hence the degree of alignment of the slots 174 with the slots 176.

Water vapor is aspirated into the oxygen stream through the aspirating nozzle 134. Drain water enters the radial opening or bore 68 adjacent the step 58, and passes back through the balance of the passageway 64 to be aspirated by the aspirating nozzle 140 and the oxygen nozzle 124 to reintroduce the drain water as water vapor into the oxygen supply.

It is contemplated that instead of simply reversing the oxygen flow by the semi-toroidal surface 168 to reduce pressure in the area of the slots 174, 176 a third pair of aspirating nozzles could be provided to achieve the desired negative pressure for introducing air into the oxygen stream.

The nebulizer which we have now described in detail is capable of being used with the special-order rigid bottles now used. However, and more importantly, it is also capable of being used with a flexible bag of water. The bag may be positioned below the nebulizer with water introduced into the float cell 98 by reduced pressure therein caused by aspiration through the nozzle 134, or the bottle may be disposed higher than the nebulizer and connected to the tapered puncturing tube 50 by means of a flexible tube, whereby water is drained from the flexible bag gravitationally into the nebulizer. In any event, inlet flow is controlled by the float 100 and the valve seat 102, whereby the correct amount of water enters the nebulizer regardless of whether the water supply is above or below the nebulizer.

The specific example of the invention herein shown and described is for illustrative purposes. Various changes in structure will no doubt occur to those skilled in the art, and will be understood as forming a part of the present invention insofar as they come within the spirit and scope of the appended claims.

The invention is claimed as follows:

1. A nebulizer for introducing water vapor into oxygen supplied to a patient comprising a body, oxygen inlet means opening into said body, oxygen outlet means from said body, aspirating means in said body and in oxygen flow relation to said oxygen inlet means, water inlet means to said body, float valve means interconnecting said water inlet means to said aspirating means to control the flow of water into the oxygen flowing through said nebulizer, said float valve means being disposed above said water inlet means, a float cell disposed below said float valve means, said float valve means including a valve seat at the upper portion of said float cell and a float member in said cell and floatable against said valve seat to close off water flow, means providing an inlet pool above said float cell and communicating therewith through said float valve means, said nebulizer further including a water passage between said water inlet means and said pool-providing means and having an upward rise, said aspirating means reducing pressure through said front cell to said pool-providing means to effect upflow of water through said water passage.

2. A nebulizer as set forth in claim 1 and further including a water aspirating nozzle, and an oxygen flow nozzle projecting oxygen across said water nozzle to aspirate water into said oxygen.

3. A nebulizer as set forth in claim 1 and further including means for collecting drain water from said oxygen outlet means, and second aspirating means connected to said drain water collecting means for aspirating drain water into the oxygen passing through said nebulizer.

4. A nebulizer as set forth in claim 2 and further including means for collecting drain water from said oxygen outlet means, and second aspirating means connected to said drain water collecting means for aspirating drain water into the oxygen passing through said nebulizer.

5. A nebulizer for introducing water vapor into oxygen supplied to a patient comprising a body, oxygen inlet means opening into said body, oxygen outlet means from said body, aspirating means in said body and in oxygen flow relation to said oxygen inlet means, water inlet means to said body, float valve means interconnecting said water inlet means to said aspirating means to control the flow of water into the oxygen flowing through said nebulizer, a water aspirating nozzle, and an oxygen flow nozzle projecting oxygen across said water aspirating nozzle to aspirate water into said oxygen, means for collecting drain water from said oxygen outlet means, and second aspirating means connected to said drain water collecting means for aspirating drain water into the oxygen passing through said nebulizer, said first mentioned aspirating means including a first oxygen nozzle directed in a predetermined direction toward said oxygen outlet means, said drain water aspirating means including a second oxygen nozzle disposed oppositely of the first oxygen nozzle.

6. A nebulizer as set forth in claim 5 and further including means for reversing the direction of oxygen flow from said second oxygen nozzle.

7. A nebulizer as set forth in claim 1 and further including means for introducing outside air into said body to dilute the flow of oxygen therethrough with air.

8. A nebulizer as set forth in claim 7 and further including a means for collecting drain water from said oxygen outlet means, and second aspirating means connected to said drain water collecting means for aspirating drain water into the oxygen passing through said nebulizer.

9. A nebulizer as set forth in claim 7 wherein said aspirating means reduces pressure in said body, and further including air bleed aperture means into said body for bleeding air into the oxygen passing therethrough.

10. A nebulizer as set forth in claim 9 and further including a shroud in which said aspirating means is mounted, said shroud tapering from a maximum diameter to a minimum exit diameter, and said air bleed means leading into the maximum diameter portion of said shroud.

11. A nebulizer as set forth in claim 9 and further including means adjacent said aperture means for adjusting the amount of air bled into the oxygen passing through said nebulizer.

12. A nebulizer for introducing water vapor into oxygen supplied to a patient comprising a body, oxygen inlet means opening into said body, oxygen outlet means from said body, aspirating means in said body and in oxygen flow relation to said oxygen inlet means, water inlet means to said body, float valve means interconnecting said water inlet means to said aspirating means to control the flow of water into the oxygen flowing through said nebulizer, means for introducing outside air into said body to dilute the flow of oxygen therethrough with air, said aspirating means reducing pressure in said body, said air introducing means including air bleed aperture means into said body, a shroud in which said aspirating means is mounted, said shroud tapering from a maximum diameter to a minimum exit diameter, said air bleed aperture means leading into the maximum diameter portion of said shroud, said aspirating means comprising a first oxygen nozzle in said shroud directed from the large diameter portion to the smaller diameter exit end, a second oxygen nozzle directed oppositely thereto, and means adjacent the large diameter portion of said shroud for reducing oxygen flow from said second nozzle.

13. A nebulizer as set forth in claim 12 wherein said flow reversing means comprises means for adjusting the amount of air bled into the oxygen flowing through said nebulizer.

* * * * *